United States Patent [19]

Kuroda et al.

[11] Patent Number: 4,791,130
[45] Date of Patent: Dec. 13, 1988

[54] MITOMYCIN DERIVATIVES AS ANTILEUKEMIA AGENTS

[75] Inventors: Tokuyuki Kuroda, Shizuoka; Koji Hisamura, Mie; Tohru Sugaya, Shizuoka; Yutaka Ohsawa, Shizuoka; Hideo Ueno, Shizuoka; Makoto Morimoto, Shizuoka; Tadashi Ashizawa, Shizuoka, all of Japan

[73] Assignee: Kyowa Hakko Kogyo Kabushiki Kaisha, Japan

[21] Appl. No.: 38,376

[22] Filed: Apr. 15, 1987

[30] Foreign Application Priority Data

Apr. 18, 1986 [JP] Japan ............................. 61-89546

[51] Int. Cl.$^4$ ...................... A61K 31/40; C07D 487/04
[52] U.S. Cl. ..................................... 514/410; 548/422
[58] Field of Search ......................... 548/422; 514/410

[56] References Cited

U.S. PATENT DOCUMENTS 4,487,769 12/1984 Vyas et al. ...................... 548/422 X Primary Examiner—Donald G. Daus
Assistant Examiner—William A. Teoli, Jr.
Attorney, Agent, or Firm—Wolder, Gross, Yavner

[57] ABSTRACT

Mitomycin derivatives having potent antitumour activity have the formula:

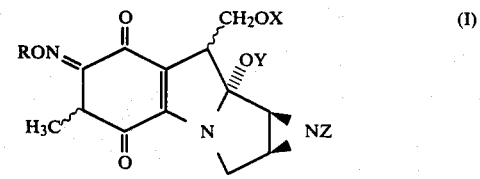

wherein
R represents lower alkyl, cycloalkyl or unsubstituted or substituted aralkyl;
X represents hydrogen or carbamoyl;
Y and Z each independently represents hydrogen or methyl;
and ⁓ represents an α or β bond.

11 Claims, No Drawings

MITOMYCIN DERIVATIVES AS ANTILEUKEMIA AGENTS

The present invention relates to novel mitomycin derivatives having antitumor activity.

Certain mitomycin compounds are known as antibiotics having antibacterial and antitumor activities. Typical examples of these compounds include mitomycin A, mitomycin B, mitomycin C and porfiromycin, which are referred to in the Merck Index, 10th Edition, mitomycin D and mitomycin E, which are disclosed in JP-A-No. 122797/79 as well as mitomycin F and mitomycin J, which are disclosed in JP-A-No. 45322/80. These mitomycin analogues shave the chemical structures shown in the following Table 1 and may be obtained by culturing a microorganism of the species *Streptomyces caespitosus*:

TABLE 1

Chemical structures of typical mitomycins

|  | $S_A$ | 9~~10 | Y | Z |
|---|---|---|---|---|
| Mitomycin A | OCH$_3$ | ◀ | CH$_3$ | H |
| B | OCH$_3$ | IIIII | H | CH$_3$ |
| C | NH$_2$ | ◀ | CH$_3$ | H |
| D | NH$_2$ | IIIII | H | CH$_3$ |
| E | NH$_2$ | IIIII | CH$_3$ | CH$_3$ |
| F | OCH$_3$ | ◀ | CH$_3$ | CH$_3$ |
| J | OCH$_3$ | IIIII | CH$_3$ | CH$_3$ |
| Porfiromycin | NH$_2$ | ◀ | CH$_3$ | CH$_3$ |

The absolute configurations are disclosed in the Journal of the American Chemical Society, 105, 7199 (1983).

Further, 10-decarbamoylmitomycins are disclosed in the Journal of Medicinal Chemistry, 14, 109 (1971).

Among these mitomycin compounds, mitomycin C is widely used for clinical purposes in view of its especially high antitumour activity. Meanwhile, various derivatives of mitomycin have been prepared to increase antitumour activity, in particular against melanoma, and/or to decrease high toxcity.

Thus, certain known derivatives of mitomycin contain a substituted amino group at the 7-position. However, only JP-A-No. 169481/85 discloses mitomycin analogues, in which the 7-amino group is substituted by a group linked through an atom other than carbon. More particularly, this prior art literature discloses mitomycin analogues in which the 7-amino group is substituted, for example, by a methanesulfonylamino group (in Example 5) or a dimethylphosphorylamino group viz. (C$_2$H$_5$)$_2$P(=S)NH— (in Example 14). However, mitomycin analogues in which the 7-amino group is modified with an O-linked substituent have not previously been reported.

The present invention now provides novel mitomycin derivatives in which the 7-amino group is substituted with an 0-linked substituent, e.g. alkoxy, aralkyloxy and the like, whereby the quinone ring is converted into e.g. a 7-alkoxyimino or 7-aralkyloxyimino- 6,7-dihydroquinone ring. These compounds have been found to exhibit excellent antitumour activity.

The present invention thus provides mitomycin derivatives having excellent antitumour activity and having the formula (I):

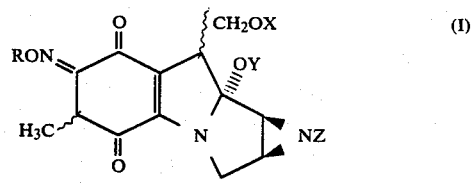

wherein
R represents lower alkyl, cycloalkyl or unsubstituted or substituted aralkyl;
X represents hydrogen or carbamoyl;
Y and Z each independently represents hydrogen or methyl;
and ∼∼represents an α or β bond.

Hereinafter, the compounds of the formula (I) are designated as Compounds (I) and compounds of other formulae are also designated similarly with reference to the formula number.

With regard to the definition of R in formula (I), lower alkyl may be a straight or branched alkyl group having 1–6 carbon atoms such as, for example, methyl, ethyl, n-propyl, isopropyl, n-butyl, iso-butyl, sec-butyl, t-butyl, n-pentyl, neopentyl, n-hexyl and the like. Suitable cycloalkyl groups include cycloalkyl groups having 3–6 carbon atoms such as, for example, cyclopropyl, cyclopentyl, cyclohexyl groups and the like. Unsubstituted or substituted aralkyl groups include, for example, benzyl, phenethyl, diphenylmethyl, trityl, substituted benzyl groups and the like. Examples of such substituted benzyl groups include those wherein the benzene ring is substituted by one or two substituents, which may be the same or different, selected from hydroxy, methoxy, halogen, amino, nitro or lower alkyl (viz. lower alkyl as specified in the definition of R in formula I).

Compounds I may be prepared by reacting a compound of formula (II):

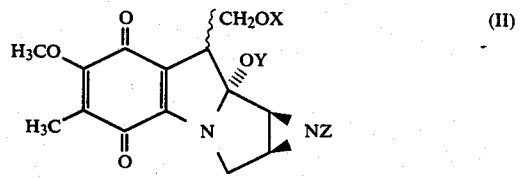

(wherein X, Y and Z are as hereinbefore defined in the above-mentioned formula I) with a compound of the formula (III):

RONH$_2$     (III)

(wherein R is as hereinbefore defined in formula I), or an acid addition salt thereof in an inert solvent. If desired, the reaction may be carried out in the presence of a base.

Examples of suitable acid addition salts of Compounds (III) include salts of hydrochloric acid, hydrobromic acid and the like. Preferred ratio of compounds (III) or acid addition salts thereof may be about 1–3 moles per mole of Compounds (II). Where an acid addition salt is used, a base may be used in an amount sufficient to liberate the Compound (III). Examples of suitable bases include sodium carbonate, potassium carbonate, sodium bicarbonate, sodium hydroxide, potassium hydroxide, lithium hydroxide and other inorganic bases; pyridine, 4-dimethylaminopyridine, triethylamine, N,N-dimethylaniline and other tertiary amines; sodium methoxide, sodium ethoxide, potassium methoxide, potassium ethoxide and other alkali metal alkoxides and the like.

Suitable inert solvents are exemplified by lower alkanols such as methanol, ethanol and isopropanol; acetonitrile; dimethylformamide; dimethylsulfoxide; tetrahydrofuran and water, any of which may be used alone or in admixture.

The reaction may preferably be carried out at a temperature of from 0° C. to 40° C., and is usually continued for a period of 5 to 30 hours.

After completion of the reaction, the Compounds (I) may be isolated by conventional techniques such as, for example, extraction, chromatography, recrystallization and various other methods known for the isolation and purification of reaction products.

Compounds (I) are new compounds and their structures are entirely distinct from the structures of the various known mitomycins and derivatives. It is believed that Compounds (I) may exist at least partially as the tautomers of formulae (IV) or (V):

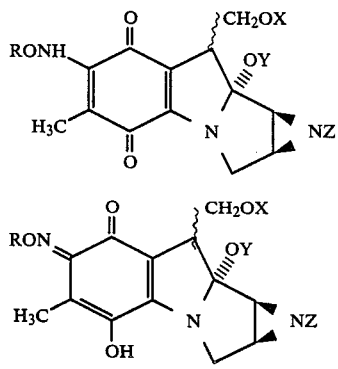

(wherein R,X,Y,Z and ∼ are as hereinbefore defined in formula I).

For example, the results obtained from $^1$H- and and $^{13}$C-NMR (in CDCl$_3$) of a compound prepared by the method described in Example 1 indicate that this compound has the structure shown by the formula (I). On the other hand, it has been confirmed that at least a proportion of the same product has the structure shown in formula (IV) or (V) in view of the fact that $^1$H-NMR of the same compound in d$_6$-dimethylsulfoxide showed a peak of 12% ($\delta$=2.01, calculated as the ratio of integral heights) of methyl qroup at the aryl position. In general, the production ratio of tautomers may vary, depending upon various factors such as the structure, conditions for measuring by NMR and the like.

It should be understood that the present invention also extends to compounds of formulae (IV) and (V) as tautomers of compounds of formula (I), and any mixture thereof.

As shown hereinafter, Compounds (I) in general have excellent antitumour activity. Certain Compounds (I) exhibit greater C.I. values than that of mitomycin C. This fact sugqests that Compounds (I) may be administered at a greater dose than mitomycin C. Moreover, as shown hereinafter the ratios of WBC$_{4000}$ to ED$_{50}$ of Compounds (I) are, in qeneral, greater than the corresponding ratio for mytomycin C. This fact suggests that their toxicities against bone marrow are superior to that of mytomycin C calculated on the doses resulting in the same ED$_{50}$.

Thus, Compounds (I) may be used for the preparation of antitumour pharmaceutical compositions comprising as active ingredient an effective amount of a Compound (I), in association with at least one pharmaceutically acceptable carrier and/or adjuvant. Thus such compositions may contain e.g. diluents, excipients, disintegrating agents, binders, lubricants, formulation bases and the like conventionally used in pharmacy.

The compounds (I) also have utility as intermediates for the preparation of other compounds having antitumour activity.

Compounds (I) may be administered in various forms. For example, when used for parenteral injection, Compounds (I) may be dissolved in liquid carriers conventionally used in the art (for example, ethanol) to which, if desired, a surfactant, solubilizing agent or the like may be added. The ethanol solution may be mixed with e.g. distilled water for injection, physiological saline, or distilled water containing fructose, mannitol etc. and the like conventionally used for such purposes. In this case, the mixture may be used with or without removal of ethanol.

It is also possible to use Compounds (I) in the form of a hypodermic powder which may be obtained by freeze-drying the ethanol solution or by mixing Compounds (I) with sodium chloride. In use, the powder is suitably dissolved. The injection may preferably be intravenous, although it is possible to administer e.g. by the intramuscular, intra-arterial, abdominal, or pleural routes.

Compositions for oral administration may be prepared in conventional manner by formulating Compounds (I), in association with suitable excipients, disintegrating agents, binders, lubricants and the like into tablets, granules or powders. Suppositories may be obtained by mixing Compounds (I) with suitable suppository bases in conventional manner.

The optimum dose may vary, depending upon the particular Compound (I), age of the patient, the symptoms and the like. However, one may e.g. administer Compounds (I) at a dosage in the range of 0.5–75 mg/60 kg.

Our invention is illustrated in the followinq Examples and Formulations. Mass spectrometry was carried out by the FAB (Fast Atom Bombardment) method.

In the Examples, the nomenclature used is illustrated by the compound of Example 1 having the following structure and designation:

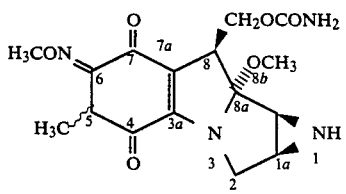

[1aS-(1aα,8β,8aα,8bα)]-8-{[(aminocarbonyl)oxy]methyl}-8a-methoxy-6-[(methoxy)imino]-5-methyl-1,1a,2,5,6,8,8a,8b-octahydro-azirino-[2′,3′:3,4]pyrrolo[1,2-a]indole-4,7-dione.

The structures of the products of Examples 1-7 are shown in Table 2.

TABLE 2

[Structure diagram showing a polycyclic compound with positions labeled: RON at position 6, C=O at 7 (labeled 7a), CH₂OX at position 9, OY at 8b, position 8a, H₃C at position 5, position 4, 3a, N at position 3, position 2, 1a, NZ]

| (Example No.) | R | 8 | 9 X | Y | Z |
|---|---|---|---|---|---|
| 1 | CH₃ | ◀ | CONH₂ | CH₃ | H |
| 2 | CH₃\CHCH₂/CH₃ | ◀ | CONH₂ | CH₃ | H |
| 3 | CH₃CH₂\CH/CH₃ | ◀ | CONH₂ | CH₃ | H |
| 4 | CH₃CH₂CH₂CH₂ | ◀ | CONH₂ | CH₃ | H |
| 5 | CH₃\CHCH₂/CH₃ | ◀ | CONH₂ | CH₃ | CH₃ |
| 6 | CH₃\CHCH₂/CH₃ | ∥∥∥∥∥ | CONH₂ | H | CH₃ |
| 7 | CH₃\CHCH₂/CH₃ | ◀ | H | CH₃ | H |

EXAMPLE 1

Preparation of [1aS-(1aα,8β,8aα)]-8{[(aminocarbonyl)oxy]methyl}-8a-methoxy-6-[(methoxy)imino]-5-methyl-1,1a,2,5,6,8,8a,8b-octahydro-azirino-[2′,3′:3,4]pyrrolo[1,2-a]indole-4,7-dione:

To sodium methoxide (0.097 g) suspended in methanol (3 ml) was added methoxyamine hydrochloride (0.154 g). The mixture is stirred at ambient temperature for 10 minutes. After addition of methanol (9 ml) and mitomycin A (0.30 g), the solution is further stirred at ambient temperature for 17 hours. The solvent is removed from the solution by evaporation under reduced pressure. The residual material is subjected to silica gel chromatography using a solvent system of chloroform/methanol (15:1 v/v) to yield the desired product (0.17 g) with a yield of 54.2%.

$^1$H-NMR (CDCl₃) δ:1.40 (d) and 1.41 (d) (3H), 2.84 (1H, m), 2.93 (1H, m), 3.21 (s) and 3.24 (s) (3H), 3.45 (1H, m), 3.73 (dd) and 3.77 (dd) (1H), 3.88 (d) and 4.24 (d) (1H), 4.09 (3H, s), 4.16 (1H, m), 4.59 (dd) and 4.65 (dd), (1H), 4.75 (dd) and 4.79 (dd) (1H), 4.89 (2H, br).

$^{13}$C-NMR (CDCl₃) δ: 17.5, 18.1, 32.4, 32.6, 36.6, 43.3, 43.9, 44.0, 49.1, 49.2, 49.9, 61.8, 62.2, 63.6, 105.7, 105.8, 125.8, 126.0, 152.2, 152.7, 152.9, 154.3, 156.7, 156.8, 176.4, 176.8, 190.7, 191.1.

IR (KBr) cm$^{-1}$: 3450, 2940, 1705, 1640, 1565, 1450, 1340, 1070, 1020 . MASS: 365 (C₁₆H₂₀N₄O₆: M.W. 364.37).

EXAMPLE 2

Preparation of [1aS-(1aα, 8β, 8aα, 8bα)]-8-{[(aminocarbonyl) oxy]methyl}-6-[(isobutyloxy)imino]-8a-methoxy-5-methyl1,1a,2,5,6,8,8a,8b-octahydro-azirino[2′,3′:3,4]pyrrolo[1,2-a]indole-4,7-dione:

Mitomycin A (0.30 g) is dissolved in methanol (30 ml). To this solution is added isobutyloxyamine hydrochloride (0.24 g). After addition of triethylamine (0.50 ml), the solution is stirred at ambient temperature for 18 hours. The solvent is removed from the solution by evaporation under reduced pressure. The residual material is subjected to silica gel chromatography using a solvent system of chloroform/methanol (20:1 v/v) to yield the desired product (0.11 g) with a yield of 29.6%.

$^1$H-NMR (CD₃OD) δ: 1.01(d) and 1.03 (d) (6H), 1.45 (d) and 1.49 (d) (3H), 2.12 (1H, m), 2.95 (1H, m), 3.06 (1H, m), 3.30 (s) and 3.33 (s) (3H), 3.74 (1H, m), 3.77 (dd) and 3.85 (dd) (1H), 3.98 (d) and 4.29 (d) (1H), 4.08 (1H, m), 4.12 (d) and 4.14 (d) (2H), 4.70 (1H, m), 4.80 (1H, m).

IR (KBr) cm$^{-1}$: 3400, 2950, 1710, 1640, 1570, 1460, 1340, 1070, 1020.

MASS: 407 (C₁₉H₂₆N₄O₆: M.W. 406.45).

EXAMPLE 3

Preparation of [1aS-(1aα, 8β, 8aα, 8bα)]-8{[aminocarbonyl) oxy]methyl}-6-[(sec-butyloxy)imino]-8a-methoxy-5-methyl-1,1a,2,5,6,8,8a,8b-octahydro-azirino [2′,3′:3,4] pyrrolo [1,2-a]indole-4,7-dione:

In a similar manner to that decribed in Example 2, the desired product (0.12 g) is obtained by using mitomycin A (0.50 g) and sec-butyloxyamine hydrochloride (0.41 g) as well as triethylamine (0.83 ml). Yield of 20.8%.

$^1$H-NMR (CDCl₃) δ: 0.90 (t) and 0.94 (t) (3H), 1.25 (d) and 1.28 (d) (3H), 1.40(d) and 1.42 (d) (3H), 1.70 (2H, m), 2.86 (1H, m), 2.93 (1H, m), 3.21 (s) and 3.24 (s) (3H), 3.45 (1H, m), 3.73 (dd) and 3.78 (dd) (1H), 3.90 (d) and 4.24 (d) (1H), 4.10 (1H, m), 4.45 (1H, m), 4.70 (1H, m), 4.76 (1H, m), 4.80 (2H, br).

IR (KBr) cm$^{-1}$: 3400, 2950, 1710, 1640, 1570, 1460, 1340, 1070, 1020.

MASS: 407 (C₁₉H₂₆N₄O₆: M.W. 406.45).

EXAMPLE 4

Preparation of [1aS-(1aα,8β, 8aα, 8bα)1-8-{[(aminocarbonyl)oxy]methyl}-6- [(n-butyloxy)imino]-8a-methoxy-5-methyl-1,1a,2,5,6,8,8a,8b-octahydro-azirino [2′,3′:3,4]pyrrolo[1,2-a]indole-4,7-dione:

In a similar manner to that described in Example 2, mitomycin A (0.42 g) and n-butyloxyamine hydrochloride (0.30 g) as well as triethylamine (0.61 ml) are used to obtain the desired product (0.12 g; yield 24.4%).

$^1$H-NMR (CD₃OD) δ: 0.95 (t) and 0.96 (t) (3H), 1.14 (2H, m), 1.70 (2H, m), 2.88 (1H, m), 2.99 (1H, m), 3.22 (s) and 3.25 (s) (3H), 3.47 (1H, m), 3.70 (dd) and 3.78 (dd) (1H), 3.93 (d) and 4.21 (d) (1H), 4.24 (1H, m), 4.27 (t) and 4.28 (t) (2H), 4.72 (1H, m), 4.78 (1H, m).

IR (KBr) cm$^{-1}$: 3400, 2940, 1710, 1640, 1570, 1460, 1340, 1070, 1020.

MASS: 407 (C₁₉H₂₆N₄O₆: M.W. 406.45).

EXAMPLE 5

Preparation of [1aS-(1aα, 8β, 8aα, 8bα)]-8-{[(aminocarbonyl)oxy]methyl}-1,5-dimethyl-6-[(isobutyloxy)imino]8a-methoxy-1,1a,2,5,6,8,8a,8b-octahydro-azirino [2',3': 3,4]pyrrolo[1,2-a]indole-4,7-dione:

Isobutyloxyamine hydrochloride (0.31 g) is dissolved in water (1.5 ml), to which anhydrous sodium carbonate (0.16 g) is added in stall portions while stirring. This solution is added to methanol(25 ml),in which mitomycin F (0.45 g) has been dissolved. The mixture is stirred at ambient temperature for 18 hours. The solvent is removed by evaporation under reduced pressure. To the residual material is added 100 ml of chloroform/methanol (9:1 v/v). The mixture is stirred for 20 minutes and filtered. The filtrate is concentrated to give an oily material which is then subjected to silica gel chromatography using a solvent system of chloroform/methanol (20:1 v/v) to yield the desired product (0.40 g) with yield of 76.8%.

$^1$H-NMR (CDCl$_3$) δ: 0.92 (d) and 0.95 (d) (6H), 1.40 (d) and 1.43 (d) (3H), 2.05 (1H, m) 2.23 (1H, m), 2.26 (3H, s), 2.32 (1H, m), 3.18 (s) and 3.22 (s) (3H), 3.40 (1H, m), 3.70 (dd) and 3.75 (dd) (1H), 3.86 (d) and 4.22 (d) (1H), 4.08 (d) and 4.10 (d) (2H), 4.16 (1H, m), 4.42 (dd) and 4.46 (dd) (1H), 4.74 (dd) and 4.80 (dd) (1H), 4.86 (2H, br).

IR (KBr) cm$^{-1}$: 3450, 2960, 1710, 1640, 1570, 1450, 1340, 1070, 1020.

MASS: 421 (C$_{20}$H$_{28}$N$_4$O$_6$: M.W. 420.46).

EXAMPLE 6

Preparation of [1aS-(1aα, 8α, 8aα, 8bα)]-8-{[(aminocarbonyl)oxy]methyl}-1,5-dimethyl-8a-hydroxy-6-[(isobutyloxy-1-imino]-1,1a,2,5,6,8,8a,8b -octahydro-azirino [2',3':3,4]pyrrolo [1,2-a]indole-4,7- dione:

In a similar manner to that described in Example 5, mitomycin B (0.52 g) and isobutylamine hydrochloride (0.31 ml) as well as anhydrous sodium carbonate (0.39 g) are used to obtain the desired product (0.20 g) with a yield of 39.7%.

$^1$H-NMR (CDCl$_3$) δ: 0.93 (d) and 0.94 (d) (6H), 1.40 (3H, d), 2.05 (1H, m), 2.23 (1H, m), 2.26 (3H, s), 2.73 (1H, m), 3.41 (1H, m), 3.74 (dd) and 3.84 (dd) (1H), 3.95 (d) and 4.24 (d) (1H), 4.07 (d) and 4.09 (d) (2H), 4.13 (1H, m), 4.70 (dd) and 4.73 (dd) (1H), 4.80 (dd) and 4.81 (dd) (1H), 4.86 (2H, br).

IR (KBr) cm$^{-1}$: 3400, 2960, 1700, 1640, 1570, 1460, 1340, 1020.

MASS: 407 (C$_{19}$H$_{26}$N$_4$O$_6$: M.W. 406.45).

EXAMPLE 7

Preparation of [1aS-(1aα, 8β, 8aα, 8bα)]-8-hydroxymethyl-6-[(isobutyloxy) imino] -8a-methoxy-5-methyl-1,1a, 2,5,6,8,8a,8b-octahydro-azirino [2',3':3,4]pyrrolo[1,2- a] indole -4,7-dione In a similar manner to that described in Example 5, decarbamoylmitomycin A (0.17 g) and isobutyloxyamine hydrochloride (0.14 g) as well as anhydrous sodium carbaonate (0.07 g) are used to obtain the desired product (0.025 g) with a yield of 12.5%.

$^1$H-NMR (CDCl$_3$) δ: 0.94 (6H, d), 1.44 (d) and 1.45 (d) (3H), 2.09 (1H, m), 2.89 (2H, m), 3.21 (s) and 3.23 (s) (3H), 3.40 (1H, m), 3.48 (1H, m), 3.91 (d) and 4.28 (d) (1H), 4.03 (1H, m), 4.09 (1H, m), 4.11 (d) and 4.14 (d) (2H), 4.16 (1H, m).

IR (KBr) cm$^{-1}$: 3450, 2960, 1635, 1570, 1460, 1020.

MASS: 364 (C$_{18}$H$_{25}$N$_3$O$_5$: M.W. 363.41).

Formulation 1

Injectable solution:

A compound prepared by the method of Example 1 (10 mg) is put into a brown vial (10 ml) under sterile conditions to obtain a sterile powder composition. Prior to use, 50% aqueous ethanol (5 ml) is added to the composition under sterile conditions. An injectable solution is obtained by dissolving the powder with vigorous stirring.

Formulation 2

Tablet:

A compound prepared by the method of Example 2 (20 mg), lactose (170 mg), potato starch (20 mg), hydroxypropylcellulose (4 mg) and magnesium stearate (1 mg) were admixed and pressed to form a tablet in conventional manner.

Formulation 3

Suppository:

A compound prepared by the method of Example 3 (20 mg), Witepsol H-15 (750 mg) and Witepsol E-75 (320 mg) are used to form a suppository in conventional manner. "Witepsol" is a Trade Mark for suppository bases commercially available from Dynamit Nobel AG of Troisdorf, Germany.

The excellent antitumour activity of Compounds (I) is apparent from the following Experiments, showing the pharmacological effects of typical Compounds (I).

Experiment 1

Table 3 indicates the effects of typical Compounds (I) against Hela S$_3$ culture cells In this Table, IC$_{50}$ denotes the concentration of the test compound capable of reducing the number of the cells to 50% of the number of untreated cells.

TABLE 3

| Effects upon Hela S$_3$ cultured cells | |
| --- | --- |
| Compound (Example No.) | IC$_{50}$ (μg/ml) |
| 1 | 0.012 |
| 2 | 0.003 |
| 3 | 0.001 |
| 4 | 0.006 |
| 6 | 0.03 |
| 7 | 0.003 |
| Mitomycin C | 0.004 |

The experiment was carried out in the following manner:

Cultured cells of Hela S$_3$ were added to a MEM medium containing 10% (V/V) of bovine fetal serum and 292 mg/ml of glutamine to obtain a cell suspension of 3×10$^4$ cells/ml. The cell suspension was poured into each well (1 ml/well) of a multiplate having 24 wells for culturing at 37° C. in an incubator containing carbon dioxide (5%) and air (95%). After 24 hours, samples were dissolved or suspended in PBS, ethanol or dimethylsulfoxide were added to the medium at different concentrations, followed by culturing at 37° C. for 72 hours in the same incubator.

An aspirator was used to collect the medium from each well. The surface of each medium was washed by added PBS (1 ml) gently, and then PBS was sucked out. PBS containing trypsin (0.05%) and EDTA (0.02%) was poured into each well. After pipetting, the number of the cells in each suspension was counted by the use of a micro-cell counter (commercial product of Toa Iyo Denshi K.K., Japan). By reference to a curve showing the concentration vs. the number of the cells, IC$_{50}$ (concentration of the sample capable of reducing the number of the cells to 50% on the basis of the number of control untreated cells) was measured.

Experiment 2

Table 4 indicates the effects of Compounds (I) upon Sarcoma 180 solid tumour. In this table, C.I. denotes chemotherapeutic index, calculated as $(LD_{50})/(ED_{50})$, wherein $LD_{50}$ denotes the value of acute toxity, and $ED_{50}$ denotes the dose of a sample which is capable of reducing the volume of Sarcoma 180 solid tumour to 50% of the corresponding volume of the solid tumour of untreated group. In this table, the value of $(WBC_{4000})/(ED_{50})$ indicates the ratio of the dose required to reduce the number of peripheral leucocytes to 4000 to $ED_{50}$, which suggests the influence upon the number of peripheral leucocytes.

TABLE 4

| Effects upon Sarcoma 180 solid tumour | | | |
|---|---|---|---|
| Compounds (Example No.) | $LD_{50}$ (mg/kg) | C.I. | $WBC_{4000}/ED_{50}$ |
| 1 | 37.5 | 0.7 | 0.5 |
| 2 | 18.8 | 3.6 | 1.9 |
| 3 | 18.8 | 3.1 | 2.4 |
| 4 | 18.8 | 2.7 | 0.9 |
| 5 | 60.0 | 3.4 | 1.4 |
| Mitomycin C | 8.4 | 1.9 | 0.6 |

$LD_{50}$, $ED_{50}$ and $WBC_{4000}$ were calculated respectively as follows:

(1) $LD_{50}$

The test compound was abdominally administered once to ddy mice, each group consisting of 5 animals. After this, the death ratio of the animals of the test group was observed for 14 days, from which $LD_{50}$ was calculated by Behrens-Körber's method.

(2) $ED_{50}$ $5 \times 10^6$ cells of Sarcoma 180 solid tumour were abdominally implanted into a ddy mouse. After 7 days, the cells were collected from the acsites fluid. The cells were washed once with physiological saline under sterile conditions and suspended in physiological saline to obtain a cell suspension containing $5 \times 10^7$ cells/ml, of which 0.1 ml was implanted into a ddy mouse (body weight $20 \pm 2$ g) under the skin of the right armpit. The test compound was dissolved in physiological saline or the same solution containing Tween 80. 24 hours after implantation of the tumour cells, 0.1-0.2 ml of the solution containing the test compound was administered to the vein at the tail of each animal of the test group consisting of 5 animals. 7 days after the implantation, the major axis (a) and minor axis (b) of the tumour were measured to calculate the volume of the tumour as "a"×"b²"/2. The antitumour effect was indicated by T/C which is the ratio of the tumour volume in the test animals to the corresponding volume of the control (untreated) animals.

T/C ratios and the dose were respectively plotted on the ordinate using an arithmetic scale and on the abscissa using a logarithmic scale, the relationship between the dosage and the T/C ratio being converted to a straight line by the least squares method. From the straight tropic line thus-obtained, the dose corresponding to a T/C=0.5 viz. $ED_{50}$ was determined.

(3) $WBC_{4000}$

Sarcoma 180 solid tumour cells ($5 \times 10^6$) were subcutaneously implanted into the skin under the right armpit of each mouse (body weight $20 \pm 2$ g) of a group consisting of 5 male mice (ddy strain). 24 hours later, a test compound was intraperitoneally administered to each animal. 4 days later, blood (0.02 ml) was collected from the suborbital plexus vein of each tumour-carrying animal. The collected sample of blood was dispersed in 9.98 ml of Cell-kit Seven solution. One drop of saponin solution was added to the sample to dissolve erythrocytes and then a microcell counter was used to measure the number of leucocytes. On graph paper, the number of leucocytes was plotted on the ordinate using an arithmetic scale, and the dosage was plotted on the abscissa using a logarithmic scale to plot the relationship of the dosage to the number of peripheral leucocytes, from which the value of $WBC_{4000}$, viz. a value capable of giving 4000 peripheral leucocytes (about half of the corresponding value in normal mice) per $mm^3$, was obtained.

What is claimed is:

1. Mitomycin compounds represented by the formula:

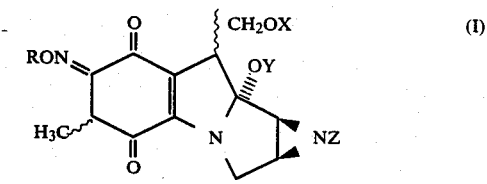

wherein R is selected from a member of the group consisting of a straight or branched alkyl having 1 to 6 carbon atoms, a cycloalkyl having 3 to 6 carbon atoms, benzyl, substituted benzyl wherein said substituent is selected from hydroxyl, methoxy, halogen, amino, nitro and $C_1$ to $C_6$ alkyl; phenethyl, diphenylmethyl and trityl; X is selected from hydrogen and carbamoyl; each of Y and Z is independently selected from hydrogen and methyl; and   is selected from $\alpha$ and $\beta$ bonds.

2. Mitomycin compounds according to claim 1 wherein R is selected from straight or branched alkyl of 1-6 carbon atoms; cycloalkyl of 3-6 carbon atoms; benzyl optionally substituted with one or two substituents selected from hydroxy, methoxy, halogen, amino, nitro and lower alkyl; phenethyl; diphenylmethyl and trityl.

3. Mitomycin compounds according to claim 2 wherein R represents alkyl of 1-4 carbon atoms.

4. Mitomycin compounds according to claim 3 wherein R is selected from n-butyl, sec-butyl and iso-butyl.

5. [1aS-(1aα, 8β, 8aα, 8bα)] -8- {[(aminocarbonyl)-oxy]methyl} -6- [(isobutyloxy) imino] -8a- methoxy-5-methyl-1, 1a,2,5,6,8,8a,8b-octahydro-azirino-[2',3':3,4]-pyrrolo-[1,2-a] indole-4,7-dione.

6. [1aS-(1aα, 8β, 8aα,8bα)]-8-{[(aminocarbonyl)oxy]-methyl}-6- [(sec-butyloxy)imino] 8a-methoxy-5-methyl-1,1a,2,5,6,8,8a,8b-octahydro-azirino-[2',3':3,4]-pyrrolo [1,2-a] indole-4,7-dione.

7. [1aS-(1aα, 8β, 8aα,8bα)]-8- hydroxymethyl-6-[(isobutyloxy) imino]-8a-methoxy-5methyl-1,1a2,5,6,8-,8a,8b-octahydro-azirino-[2',3':3,4] pyrrolo [1,2-a] indole-4,7-dione.

8. [1aS-(1aα, 8β, 8aα,8bα)] -8 -{[(aminocarbonyl)oxy]methyl} -6-[(n-butyloxy) imino] -8a- methoxy-5-methyl-1,1a,2,5,6,8,8a,8b-octahydro-azirino [2',3':3,4]pyrrolo [1,2-a] indole-4,7-dione.

9. [1aS-(1aα, 8β, 8aα,8bα)] -8-{[(aminocarbonyl)oxy]-methyl}-1,5-dimethyl-6-[(iso-butyloxy)    imino]-8a- methoxy-1,1a,2,5,6,8, 8a,8b-octahydro-azirino-[2′,3′:3,4] pyrrolo [1,2-a] indole-4,7-dione.

10. An antileukemia composition comprising a pharmacologically effective amount of a mitomycin compound according to claim 1 in association with at least one pharmaceutically acceptable carrier and/or adjuvant.

11. A process for treating leukemia in a mammal with a pharmaceutically effective amount of a mitomycin compound according to claim 1.

* * * * *